(12) United States Patent
Lin (10) Patent No.: US 10,709,731 B2
(45) Date of Patent: Jul. 14, 2020

(54) MATERIALS FOR TREATING AND PREVENTING MUCOSA RELATED DISEASE

(71) Applicant: AIHOL CORPORATION, Las Vegas, NV (US)

(72) Inventor: Shyh-Shyan Lin, Taipei (TW)

(73) Assignee: AIHOL CORPORATION, Las Vegas, NV (US)

( * ) Notice: Subject to any disclaimer, the term of this patent is extended or adjusted under 35 U.S.C. 154(b) by 0 days.

(21) Appl. No.: 15/248,146

(22) Filed: Aug. 26, 2016

(65) Prior Publication Data

US 2016/0361347 A1 Dec. 15, 2016

Related U.S. Application Data

(63) Continuation of application No. 13/996,952, filed as application No. PCT/US2012/045259 on Jul. 2, 2012, now abandoned.

(30) Foreign Application Priority Data

Jul. 12, 2011 (EP) .................................... 11173628

(51) Int. Cl.
  *A61K 31/728* (2006.01)
  *A61K 45/06* (2006.01)
  *A61K 47/61* (2017.01)
  *A61K 39/39* (2006.01)

(52) U.S. Cl.
  CPC ............ *A61K 31/728* (2013.01); *A61K 39/39* (2013.01); *A61K 45/06* (2013.01); *A61K 47/61* (2017.08); *Y02A 50/491* (2018.01)

(58) Field of Classification Search
  CPC .............................. A61K 31/728; A61K 39/39
  USPC ................................. 514/54; 536/123.1, 55.1
  See application file for complete search history.

(56) References Cited

U.S. PATENT DOCUMENTS

| | | | |
|---|---|---|---|
| 5,888,986 A | 3/1999 | Morales et al. | |
| 6,107,347 A | 8/2000 | Francese et al. | |
| 6,608,043 B1* | 8/2003 | Serizawa ............ | A61K 31/728 514/494 |
| 7,354,910 B2 | 4/2008 | Kono | |
| 2003/0171332 A1 | 9/2003 | Abraham et al. | |
| 2004/0041440 A1 | 3/2004 | Weiss et al. | |
| 2004/0071740 A1 | 4/2004 | Petrigni et al. | |
| 2004/0198695 A1 | 10/2004 | Anhu et al. | |
| 2005/0080037 A1 | 4/2005 | Petrella | |
| 2005/0107330 A1 | 5/2005 | Greve et al. | |
| 2009/0163441 A1* | 6/2009 | Gobbo ................. | A61K 31/728 514/54 |
| 2010/0028399 A1* | 2/2010 | Hornof .................. | A61K 8/735 424/422 |
| 2011/0166098 A1 | 7/2011 | Wu | |
| 2011/0166099 A1 | 7/2011 | Wu | |
| 2011/0166100 A1 | 7/2011 | Wu | |

FOREIGN PATENT DOCUMENTS

| | | | |
|---|---|---|---|
| BE | 904547 | 10/1986 | |
| CN | 101534842 | 9/2009 | |
| CN | 102114031 | 7/2011 | |
| EP | 1369119 | 12/2003 | |
| EP | 2251016 | 11/2010 | |
| EP | 2289522 | 3/2011 | |
| EP | 2292243 | 3/2011 | |
| JP | 10513476 | 12/1998 | |
| JP | 2004513071 | 4/2004 | |
| JP | 2005145963 | 6/2005 | |
| JP | 2011037853 | 2/2011 | |
| WO | 8705517 | 9/1987 | |
| WO | WO 9635721 A1 * | 11/1996 | ......... A61K 47/4823 |
| WO | 9703699 | 2/1997 | |
| WO | WO 0044367 A2 * | 8/2000 | ........... A61K 9/0014 |
| WO | 2013006548 | 1/2013 | |

OTHER PUBLICATIONS

Jeong et al.; KR 2008074583 A; Aug. 13, 2008 (Machine English Translation).*
Delpech, et al., Hyaluronan: fundamental principles and applications in cancer, Journal of Internal Medicine, (1997): 242: 41-48, Blackwell Science Ltd.
Teder, et al., Resolution of Lung Inflammation by CD44, Science AAAS, (2002), 296, 155, DOI: 10.1126/science.1069659.
Richards, et al., Conjuctivitis, Pediatrics in Review, (May 2010), vol. 31, No. 5: 196-208, University of Michigan.
Bousquet, et al., Allergic rhinitis management pocket reference 2008*, Allergy, (2008): 63, 990-996. The Authors, Journal compilation, Blackwell.
Casiglia, et al., Aphthous stomatitis, (2006): Emedecine (website).
Oohen, et al., Infectious Diseases, (2004): 2nd ed., Chaper 33: Bronchitis, Bronchiectasis, and Cystic Fibrosis, Elsevier.
Devault, et al., Updated Guidelines for the Diagnosis and Treatment of Gastroesophageal Reflux Disease, The American Journal of Gastroenterology, (1999): vol. 94, No. 6, Am. Coll. of Gastroenterology, Elsevier Science Inc.
Kapoor, et al., Topical hyaluronic acid in the management of oral ulcers, (2011): vol. 56, 3, 300-302, Indian Journal of Dermatology.
Soldati, et al., Mucosal wound healing after nasal surgery. A controlled clinical trial on the efficacy of hyaluronic acid containing cream, Drugs Under Experimental and Clinical Research, (1999): 25, (6): 253-261.

(Continued)

*Primary Examiner* — Shaojia A Jiang
*Assistant Examiner* — Michael C Henry
(74) *Attorney, Agent, or Firm* — PATENTTM.US (57) ABSTRACT

Provided is a hyaluronic acid (HA) composition for use in treating or preventing mucosa related disorders or diseases including a mixture of HAs having different average molecular weights and different rheological, isolation, tissue scaffold and degradation properties. The resulting formulation demonstrates an optimal balance between adhesion, tissue scaffold and treating time on the treatment and prevention of mucosa related disorders or diseases including conjunctivitis, otitis, allergic rhinitis, gingivitis, oral ulcer, bronchitis, gastroesophageal reflux disease (GERD), esophagitis, gastritis, enteritis, peptic ulcer, inflammatory bowel disease (IBD), irritable bowel syndrome (IBS), urethritis, cystitis and vaginitis.

6 Claims, 7 Drawing Sheets

(56) References Cited

OTHER PUBLICATIONS

Gonzalez, et al., Protective effect on the urinary bladder mucosa of intravesical hyaluronic acid in cervix cancer patients treated with pelvic radiotherapy, weekly chemotherapy and high-dose-rate brachytherapy, Brachytherapy (2008): vol. 7, No. 2, 91-194, pp. 152-153.

Fu, et al., Inhibition of Experimental Allergic Rhinitis by the n-Butanol Fraction from the Anamalous Fruits of Gleditsia sinensis, Biol. Pharm. Bull. (2003): vol. 26, No. 7, 974-977, Pharmaceutical Society of Japan.

* cited by examiner

MATERIALS FOR TREATING AND PREVENTING MUCOSA RELATED DISEASE

BACKGROUND OF THE INVENTION

1. Field of the Invention

The present invention provides a composition of hyaluronic acids for treating and preventing mucosa related disorders or diseases whereas the symptoms include ulceration, inflammation, allergic reaction and bleeding.

2. Description of the Prior Arts

Hyaluronic acid, also known as hyaluronan, hyaluronate and sodium hyaluronate, is generally referred to as HA, which is a natural glycosaminoglycan macromolecule including disaccharides composed of the alternative N-acetyl-D-glucosamine and D-glucuronic acid linked via alternative β-1,3 and β-1,4 glycosidic bonds. HA found in nature with a molecular weight (Mw) between 50,000 Dalton (Da) and a few million Dalton usually has high viscosity.

HA found in nature is the fluid with elasticity, filling between the cells and the collagenous fibers and covering onto some epidermal tissues, mainly for protecting and lubricating cells, for providing a platform for transporting the regulatory T cell, and also for stabilizing collagen network and protecting collagen network from the mechanical damage. HA is also a major lubricant in the tendon and the tendon sheath and on the surface of the synovial membrane due to its lubricant feature and being a high shock absorber, and HA is helpful for the tissue rheological mechanics, motion and the cell proliferation (referring to Delpech, B. et al., 1997, Hyaluronan: fundamental principles and applications in cancer. *J. Intern. Med.* 242, 41-48), and participates in the receptor interaction on the surface of some cells, particularly to be the major receptor of CD44. CD44 is widely accepted as a marker of the activated lymphocyte (referring to Teder P, et al., 2002, Resolution of lung inflammation by CD44. *Science*, 296: 155-158).

Recently, HA is applied in clinical treatment in the sodium salt form mainly in eye, skin, orthopedics, surgery, arthritis, artery treatment and in cosmetic fields. The HA with alkali metal ion, alkaline earth metal ion (for example the magnesium ion), aluminum ion, ammonium ion, and salt form of the replacement of the ammonium ion can be the carrier for assisting drug absorption (referring to Belgium Patent 904, 547). The silver salt is used as the mycocide and the gold salt is used for treating the rheumatoid arthritis among the heavy metal salt of the HA (referring to WO 87/05517).

U.S. Pat. No. 5,888,986 discloses a method and related structure for using HA at an effective concentration to treat cystitis, wherein the average Mw of the HA is more than 200,000 Da. There is only one species of HA with a certain Mw been applied in the embodiment thereof. For example, HA with the average molecular weight of 650 kDa or 1,900 kDa is used to treat the cystitis; however, the single species of HA with the certain average molecular weight cannot be used for both prompt treatment and sustained effect. US patent application 2005/0080037 discloses the use of HA for treating acute and overuse sprain and the reaction thereof, wherein the Mw of the HA is only between 900 KDa and 1200 KDa, and the single species of HA with the certain average Mw cannot perform both prompt healing and prolonged action.

U.S. Pat. No. 7,354,910 discloses that the hyaluronic acid and hyaluronate with Mw between 600 KDa and 1,200 KDa can be applied to treat inflammatory bowel disease (IBD). However, hyaluronic acid and hyaluronate with merely one average molecular weight could not cover both the immediate and sustained functions in the treating effect after being injected into the patient, therefore, it is very inconvenient for patients clinically.

European patent 1369119 discloses the use of HA for treating autoimmune disease with HA with Mw of 0.6 MDa to 3 MDa. However, the referenced patent only uses one species of HA with a certain average molecular weight, lacking in both quick and long term effects simultaneously.

The mucous membranes (or mucosae; singular mucosa) are linings of mostly endodermal origin, covered in epithelium, and involved in absorption (gastrointestinal tract) and secretion (gastrointestinal and respiratory tract). They line cavities that are exposed to the external environment and internal organs and contiguous with the skin at several body areas: at the nostrils, the mouth, the lips, the eyelids, the ears, the genital area, and the anus. The sticky, thick fluid secreted by the mucous membranes and glands is termed mucus. The term mucous membrane refers to where they are found in the body and not every mucous membrane secretes mucus.

Eye

Conjunctivitis refers to inflammation of the conjunctiva (the outermost layer of the eye and the inner surface of the eyelids). It is most commonly due to an infection or an allergic reaction (referring to Richards A, May 2010. "Conjunctivitis". *Pediatr Rev* 31 (5): 196-208).

Ear

Otitis is a general term for inflammation or infection of the ear, in both humans and other animals. It is subdivided into: Otitis externa that involves the outer ear and ear canal; otitis media that involves the middle ear; otitis interna that involves the inner ear.

Allergic Rhinitis

Rhinitis is defined as inflammation of the nasal membranes and is characterized by a symptom complex that consists of any combination of the following: sneezing, nasal congestion, nasal itching, and rhinorrhea. The eyes, ears, sinuses, and throat can also be involved. Allergic rhinitis is the most common cause of rhinitis and affects approximately 20% of the population. While allergic rhinitis is not a life-threatening condition, complications can occur and the condition can significantly impair quality of life, which leads to a number of indirect costs (referring to Bousquet J et al. Allergic rhinitis management pocket reference 2008. Allergy 2008 August; 63 (8):990-996). US patent application 20050107330 discloses a pharmaceutical composition for curative topical treatment of rhinitis comprising at least one acidic glycosaminoglycan. However, this invention also contains at least one sympathomimetic suitable for topical application and having vasoconstrictor action or detumescent action on the mucous membrane or its physiologically acceptable salts or derivatives. Therefore, it did not disclose or teach combining HAs with two different average molecular weights.

Mouth

Oral mucosa is the mucous membrane epithelium of the mouth. An oral ulcer is an open sore inside the mouth, or, in rare cases, a break in the mucous membrane or the epithelium on the lips or surrounding the mouth. The types of ulcers are diverse, with a multitude of associated causes including: physical abrasion, acidic fruit, infection, other medical conditions, medications, and cancerous and non-specific processes. Once formed, the ulcer may be maintained by inflammation and/or secondary infection. Two common types are aphthous ulcers ("canker sores") and cold sores (fever blisters, oral herpes). Cold sores around the lip are caused by viruses (referring to J. M. Casiglia, et al., October 2006. "Aphthous stomatitis". Emedicine (website)).

Bronchitis

Bronchitis is inflammation of the mucous membranes of the bronchi, the airways that carry airflow from the trachea into the lungs. Bronchitis can be divided into two categories, acute and chronic, each of which has unique etiologies, pathologies, and therapies. Acute bronchitis often occurs during the course of an acute viral illness such as the common cold or influenza. Chronic bronchitis most often develops due to recurrent injury to the airways caused by inhaled irritants. Cigarette smoking is the most common cause, followed by air pollution and occupational exposure to irritants (Cohen, Jonathan and William Powderly. Infectious Diseases. 2nd ed. Mosby (Elsevier), 2004. "Chapter 33: Bronchitis, Bronchiectasis, and Cystic Fibrosis"). US patent application 20030171332 discloses a method of treating respiratory conditions by a polysaccharide capable of binding CD44. However, only one single species of HA can be involved.

Gastrointestinal Mucosa

The mucosa is the innermost layer of the gastrointestinal wall that is surrounding the lumen, or open space within the tube. This layer comes in direct contact with food bolus, and is responsible for absorption, digestion, and secretion which are the important processes in digestion.

The mucosae are highly specialized in each organ of the gastrointestinal tract, facing a low pH in the stomach, absorbing a multitude of different substances in the small intestine, and also absorbing specific quantities of water in the large intestine. Reflecting the varying needs of these organs, the structure of the mucosa can consist of invaginations of secretory glands (e.g., gastric pits), or it can be folded in order to increase surface area.

The gastrointestinal mucosa forms a barrier between the body and a lumenal environment which not only contains nutrients, but is laden with potentially hostile microorganisms and toxins. The challenge is to allow efficient transport of nutrients across the epithelium while rigorously excluding passage of harmful molecules and organisms into the animal. The exclusionary properties of the gastric and intestinal mucosa are referred to as the "gastrointestinal barrier". In general, toxins and microorganisms that are able to breach the single layer of epithelial cells have unimpeded access to the systemic circulation.

Gastroesophageal reflux disease (GERD) is chronic symptoms or mucosal damage caused by gastric acid coming up from the stomach into the esophagus. A typical symptom is heartburn. GERD is usually caused by changes in the barrier between the stomach and the esophagus, including abnormal relaxation of the lower esophageal sphincter, which normally holds the top of the stomach closed; impaired expulsion of gastric reflux from the esophagus, or a hiatal hernia. These changes may be permanent or temporary ("transient") (referring to DeVault K R, 1999. "Updated guidelines for the diagnosis and treatment of gastroesophageal reflux disease. The Practice Parameters Committee of the American College of Gastroenterology". *Am J Gastroenterol* 94 (6): 1434-42).

Peptic Ulcer

As generally known a peptic ulcer and also known as PUD or peptic ulcer disease, peptic ulcer is an ulcer (defined as mucosal erosions equal to or greater than 0.5 cm) of an area of the gastrointestinal tract that is usually acidic and thus causes extreme pain Almost 70-90% of ulcers are associated with *Helicobacter pylori*, a spiral-shaped bacterium that lives in the acidic environment of the stomach. Ulcers can also be caused or worsened by drugs such as aspirin, Plavix (clopidogrel), ibuprofen, and other NSAIDs (non-steroid anti-inflammatory drugs).

Contrary to general belief, peptic ulcers arise more in the duodenum (first part of the small intestine, just after the stomach) rather than in the stomach. About 4% of stomach ulcers are caused by a malignant tumor, so multiple biopsies are needed to exclude cancer. Duodenal ulcers are generally benign. The classification of peptic ulcer by region or location includes: Stomach (called gastric ulcer); Duodenum (called duodenal ulcer); Esophagus (called esophageal ulcer); Meckel's Diverticulum (called Meckel's Diverticulum ulcer).

The above embodiments all stand for mucosa related disorder or disease but are not limited to aforementioned. The disclosed disorders or diseases may be treated by different drugs or therapies so far. However, such treatments are mostly achieved by drug with complicated composition through highly specialized preparation processes and not by a simple and safe treatment. No prior art except the inventor of the present invention taught or predicted combining two species of HA with two different average molecular weights (LMWHA and HMWHA) separated by 1.5 million Da, which means a person skilled in the art cannot induce the concept of the utility of the mixture by combining any other prior arts.

SUMMARY OF THE INVENTION

To overcome the shortcomings, the present invention provides a method of treating mucosa related disorder by administering to a subject in need thereof a therapeutically effective amount of a mixture of hyaluronic acid comprising at least two hyaluronic acid compositions to mitigate or obviate the aforementioned problems.

An object of the present invention is to use the biological activity of at least two species of hyaluronic acids with different average molecular weights or the pharmaceutically acceptable salt thereof to treat mucosa related disorder or disease. The low average molecular weight hyaluronic acid (LMWHA) and the high average molecular weight hyaluronic acid (HMWHA) have different viscosity, function of insulation and degradation rates. The hyaluronic acid with an average Mw lower than 1.5 million Da is categorized as LMWHA, and the hyaluronic acid with an average Mw higher than 1.5 million Da is categorized as HMWHA. Thus, mixture of LMWHA and HMWHA can form a desired composition, wherein the LMWHA can rapidly cover the inflammatory surface to treat and prevent mucosa related disorder or disease (for example, conjunctivitis, otitis, allergic rhinitis, gingivitis, oral ulcer, bronchitis, gastroesophageal reflux disease (GERD), esophagitis, gastritis, enteritis, peptic ulcer, inflammatory bowel disease (IBD), irritable bowel syndrome (IBS), urethritis, cystitis or vaginitis), and the HMWHA can prolong the degradation in order to achieve a longer effective period. Thus, a faster treatment and a sustained release effect may be achieved.

Accordingly, the present invention provides a composition for use on a mammal or a human in treating or preventing a mucosa related disorder or disease comprising:

a therapeutically effective amount of a hyaluronic acid mixture (HA mixture) including a low average molecular weight hyaluronic acid (LMWHA) and a high average molecular weight hyaluronic acid (HMWHA), wherein the average molecular weight (Mw) of LMWHA is between 50 kilo Da and 1.5 million Da, and the average Mw of HMWHA is between 1.5 million Da and 5 million Da, wherein the average molecular weight of LMWHA is apart from the average molecular weight HMWHA by at least 0.5 million Da, and a mixing ratio of the LMWHA to the HMWHA is in a range from 20:80 to 80:20 by weight.

Other objectives, advantages and novel features of the invention will become more apparent from the following detailed description when taken in conjunction with the accompanying drawings.

The scenario of the present invention is introduced in the prologue of degradation of hyaluronic acid (HA) by hyaluronidase (HAase). The linear (LMWHA) or globular HA (HMWHA) is degraded into small fragments whereas the globular HA can compensate for the linear one to contribute to the treatment effect so as to prolong the action time. It has been well known that HAase activity can be used as a marker of inflammation as briefed below. Accordingly, combination of low average and high average molecular weight (Mw) HAs is utilized to proceed with treatment effect accompanied by long-term action. Therefore, the loss of shorter HA can be sustained supplied result in continues wound healing or providing a soft barrier to isolate a protected tissue from damage. Hereinafter will be the detail description of the scenario.

Figure 1:
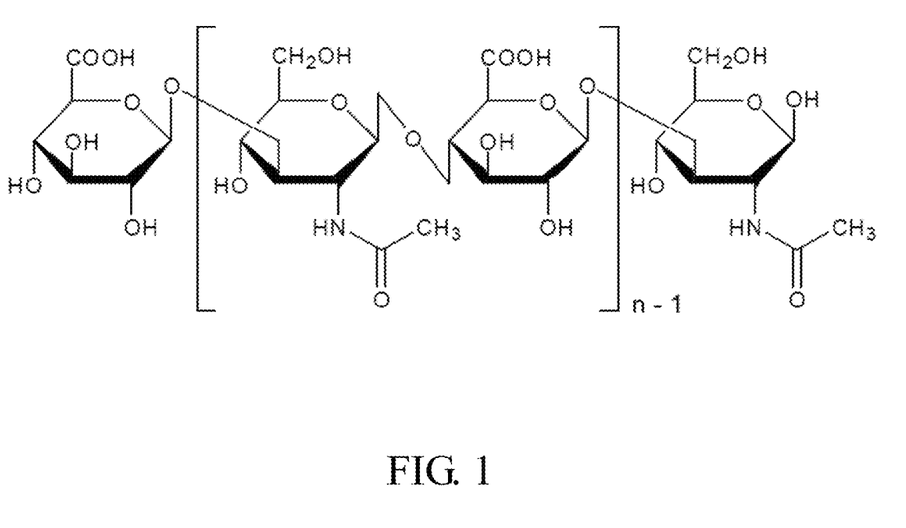
FIG. 1 shows the general chemical structure of hyaluronic acid.

The composition in accordance with the present invention used to treat and prevent mucosa related disorder or disease comprises a therapeutically effective amount of a HA mixture including a low average molecular weight hyaluronic acid (LMWHA) and a high average molecular weight hyaluronic acid (HMWHA). Low average Mw HA is based on its repeated disaccharide units to form a linear structure (FIG. 1); however, in the high average Mw HA, by the reaction of hyaluronic acid with an amine, it is believed that the carboxylic groups of the linear hyaluronic acid macromolecule react with the di/tri/poly amines to form an amide linkage and form an inter- or intra-molecular bridge. Due to this reaction, the starting coiled hyaluronic acid structure is transformed into a globular spherical nanoparticle (U.S. Pat. No. 7,879,818). Different molecular weights have different rheology, adhesion, functions of tissue scaffold and degradation in the solution, and therefore, the hyaluronic acid mixture can balance the drug effect and the degradation rate in order to treat and to prevent mucosa related disorder or disease, as well as to achieve a proper and prolonged treatment effect.

Tranchepain F et al. disclose that HA has different biological functions according to its molar mass. Physicochemically, studies of native HA hydrolysis catalyzed by bovine testicular HAase have suggested that kinetic parameters depend on HA chain length. HA hydrolysis catalyzed by HAase was used in a new procedure to obtain HA fragments of different molar masses (Tranchepain F et al., A complete set of hyaluronan fragments obtained from hydrolysis catalyzed by hyaluronidase: Application to studies of hyaluronan mass distribution by simple HPLC devices. *Anal Biochem.* 2006 Jan. 15; 348(2): 232-42) Similarly, the same research group also discloses that HA has various biological functions that are strongly dependent on its chain length. HA hydrolysis catalyzed by HAase is believed to be involved in the control of the balance between longer and shorter HA chains. Shorter HA chains seem to be too short to form a stable complex and longer HA chains also encounter difficulties in forming a complex, probably because of steric hindrance.

Several reports describe that HAase is involved in inflammation. Synovial fluid (SF) HAase activity could be used as a marker of synovial inflammation (Nagaya H et al., Examination of synovial fluid and serum HAase activity as a joint marker in rheumatoid arthritis and osteoarthritis patients. *Ann Rheum Dis.*, 1999, 58(3): 186-8). HA is a major component of the extracellular matrix of periodontal ligament (PDL) contributing to the structural and functional integrity. HA contributes to the buffering effect of the PDL during chewing, and they are also important in inflammation and wound healing. The study suggests that PDL fibroblast expresses HAase and generates HAase activity essential for extracellular HA metabolism under physiological and inflammatory conditions (Ohno S et al., Expression and activity of hyaluronidase in human periodontal ligament fibroblasts. *J Periodontol.*, 2002, 73(11): 1331-7). Short HA fragments catalyzed by HAase are involved in inflammation processes and angiogenesis, whereas native HA is not (Tranchepain F et al., Supra).

Pursuant to the present invention, HA with an average molecular weight lower than 1.5 million Da is categorized as LMWHA, the preferred range of the average molecular weight is between 50 kilo Da and 1.5 million Da, the more preferred range of the average molecular weight is between 0.1 million and 1.5 million Da, and the most preferred range of the average molecular weight is between 0.1 million and 0.5 million Da. HA with an average molecular weight higher than 1.5 million Da is categorized as HMWHA, the preferred range of the average molecular weight is between 1.5 million and 5 million Da, and the most preferred range of the average molecular weight is between 1.5 million and 2.5 million Da. When the composition containing a mixture of LMWHA and HMWHA is administered to a subject in need thereof, the LMWHA promptly covers the inflammatory portion to treat and prevent mucosa related disorder or disease, meanwhile the HMWHA extends the treatment effect of the LMWHA. Thus, treatment is promptly achieved and release effect is sustained. The general chemical structure of the HA may be illustrated as in FIG. 1.

The species of HA is not only being shown as Mw but also as intrinsic viscosity ($\eta$) which is directly related to the Mw of a polymer through the Mark-Houwink-Sakurada (MHS) equation: $[\eta]=KM\alpha$. For hyaluronic acid, K is 0.00057 and the exponent $\alpha$ is 0.75 at the following conditions: 0.15 M NaCl in phosphate buffer, pH 7.5, 20 ("Standard Guide for Characterization and Testing of Hyaluronan as Starting Materials Intended for Use in Biomedical and Tissue Engineered Medical Product Applications", ASTM Designation: F 2347-03).

Figure 2:
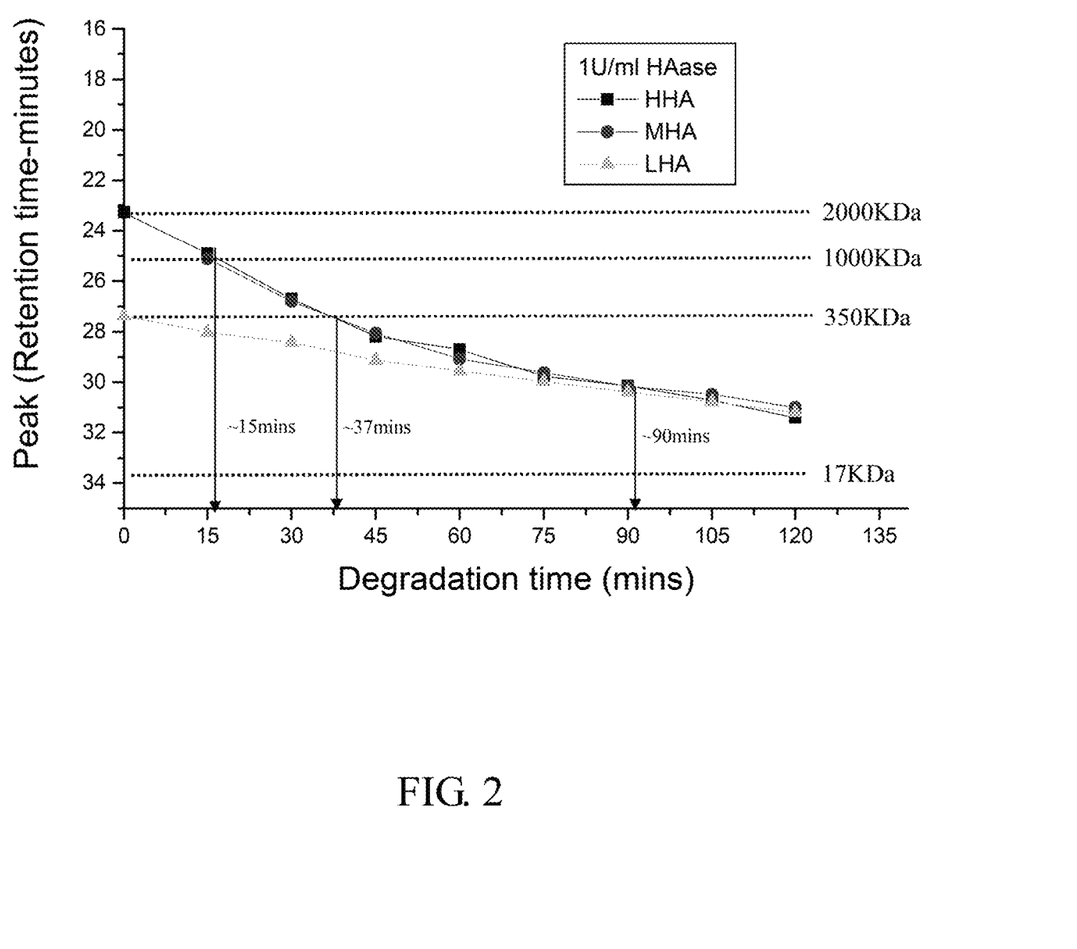
FIG. 2 shows the retention time of HAs by GPC diagram, wherein the vertical axis represents the retention time in GPC, and the horizontal axis represents the degradation time of HA in a solution containing HAase.
Figure 3:
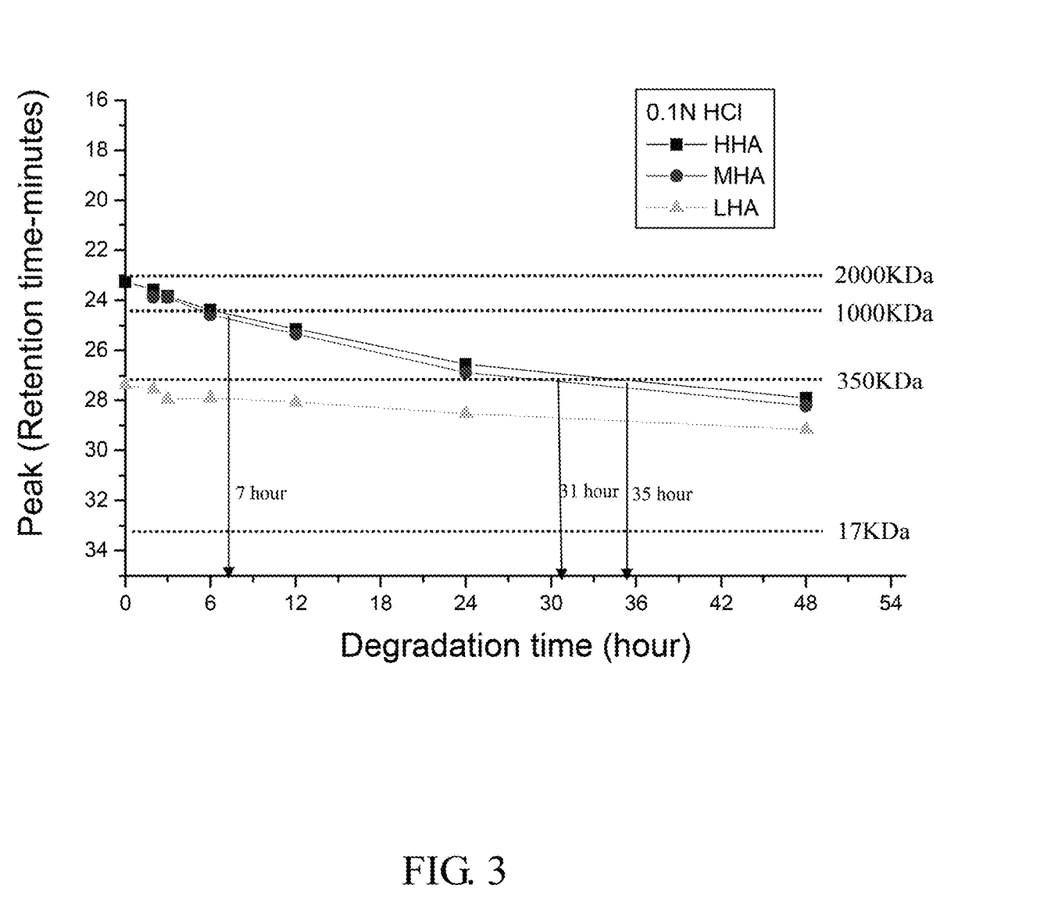
FIG. 3 shows the retention time of HAs by GPC diagram, wherein the vertical axis represents the retention time in GPC, and the horizontal axis represents the degradation time of HA in artificial gastric juice.

The present invention provides results showing that high average Mw HA can compensate for low average Mw HA even under action of HAase (FIG. 2) or artificial gastric juice (FIG. 3). The results indicate that HA can be replenished in the situation where HAase exists or in the gastrointestinal environment to keep a long-term effect. The retention time was obviously increased with the increased degradation of all three HAs under HAase (FIG. 2). The retention time was slowly increased with the increased degradation of all three HAs under acid environment (FIG. 3). The simulated physiological situations were used to proceed in experimental parameters, but true physiological environments are more complicated that may cause slightly different result. However, the trend of HA degradation will not be changed owing to its natural molecular characteristic that high average Mw HA can compensate for low average Mw HA.

Another preferred embodiment of the composition in accordance with the present invention includes, but not limited to, a 1:1 (w/w) mixture of LMWHA and HMWHA by weight in a salt form of HA, and a more preferred embodiment of the ratio of LMWHA to HMWHA may be adjusted depending on the clinical purpose to be between 20:80 and 80:20 by weight. The HA mixture with a higher ratio of LMWHA to HMWHA can be more helpful in speeding up the treatment; on the contrary, a higher ratio of HMWHA to LMWHA can provide a longer degradation time to prolong the overall treatment effect.

The term mucosa used herein includes, but not limited to, the mucosa of an eye, the mucosa of an ear, the mucosa of a nose, the mucosa of a mouth, the mucosa of a respiratory tract, the mucosa of a gastrointestinal tract, the mucosa of a urinary tract and the mucosa of a genital tract, whereas mucosa related disorder or disease of the present invention comprises symptoms of ulceration, inflammatory, allergic reaction or bleeding. The preferred embodiment of the mucosa related disorder or disease includes, but not limited to, conjunctivitis, otitis, allergic rhinitis, gingivitis, oral ulcer, bronchitis, gastroesophageal reflux disease (GERD), esophagitis, gastritis, enteritis, peptic ulcer, inflammatory bowel disease (IBD), irritable bowel syndrome (IBS), urethritis, cystitis and vaginitis. The more preferred embodiment of enteritis includes, but not limited to, acute enteritis, chronic enteritis, infectious enteritis, ischemic enteritis, radioenteritis and drug induced enteritis. The more preferred embodiment of peptic ulcer includes, but not limited to, gastric ulcer, duodenal ulcer, esophageal ulcer and Meckel's Diverticulum ulcer. The more preferred embodiment of IBD includes, but not limited to, Crohn's disease and ulcerative colitis. The more preferred embodiment of IBS includes, but not limited to, coeliac disease, fructose malabsorption, mild infections, parasitic infections like giardiasis, functional chronic constipation and chronic functional abdominal pain.

Figure 4:
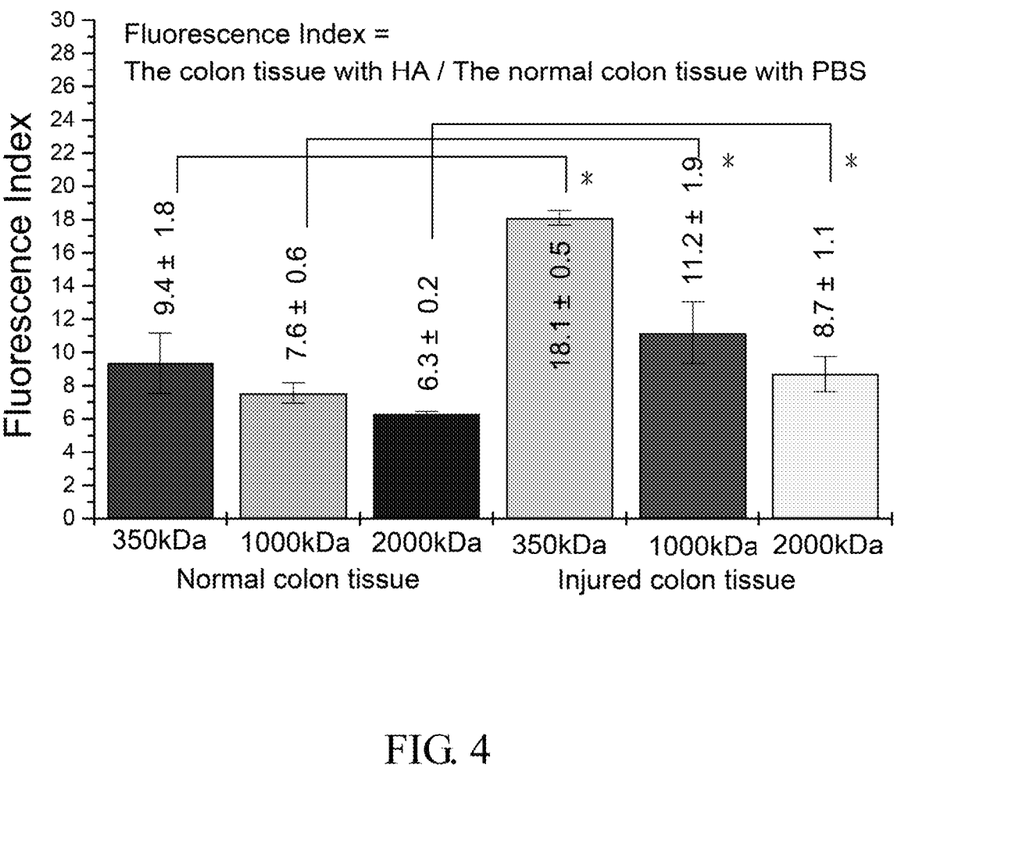
FIG. 4 shows the affinity of HAs by fluorescent index in normal and injured colon tissues.

The result of the present invention shows that the HAs with the same average Mw were absorbed in the injured colon tissues obviously higher than in the normal colon tissues ($P<0.01$, FIG. 4). Comparing the differences among HAs of three average molecular weights absorbed in the injured colon tissues, the fluorescent index of absorption of 350 KDa HA by the injured colon tissues was obviously higher than the HAs of the other two average molecular weights (2000 kDa and 1000 kDa). Further, the fluorescent index of absorption of 1 MDa HA by even normal or injured colon tissues was higher than 2000 kDa HA. This result explains fast dispersed and covered effect of low Mw HA which supplies instant wound healing and protection of the tissue from being injured further. Combining the aforementioned data, the present invention provides a method of fast and constant treatment or prevention of mucosa related disorder or disease.

Another preferred embodiment of the composition in accordance with the present invention further includes an excipient to formulate an administrating dosage form for eye, ear, oral, nose, respiratory tract, gastrointestinal tract or topical use. The more preferred embodiment of the administrating dosage form for oral use is selected from the group consisting of solid dosage form, solution including, but not limited to suspension, tablet including, but not limited to controlled-release tablet, and capsule including, but not limited to enteric-coated capsule. The most preferred embodiment of the solid dosage form is orally administered at a dose of between 50 mg and 1000 mg per day. The more preferred embodiment of the administrating dosage form for gastrointestinal tract use is selected from the group consisting of solid dosage form, perfusion, enema, suppository, and solution including, but not limited to suspension. The more preferred embodiment of the administrating dosage form for topical use is selected from the group consisting of perfusion, enema, suppository, spray, inhalation, and drop.

The preferred embodiment of treating allergic rhinitis or bronchitis can be carried out by administrating the composition of the present invention as an adjuvant conjunctively used with a drug of antihistamine, antiallergics, anticongestives, steroid or antiasthma to a subject in need thereof. The preferred embodiment of treating enteritis can be carried out by administering the mixture of the present invention as an adjuvant conjunctively used with a drug of antibiotic or antispasmodic to a subject in need thereof. The preferred embodiment of treating peptic ulcer can be carried out by administering the mixture of the present invention as an adjuvant conjunctively used with a drug of coagulant, antibiotics, antacid, H2 blocker, potassium hydrogen ion pump blocker (PPI), cytoprotectives or mucosa protector to a subject in need thereof. The preferred embodiment of treating IBD can be carried out by administering the mixture of the present invention as an adjuvant conjunctively used with a drug of steroid, immunosuppressive agent, antibiotic, 5-ASA (5-aminosalicylic acid) and derivatives, or anti-inflammatory to a subject in need thereof.

Figure 5A:
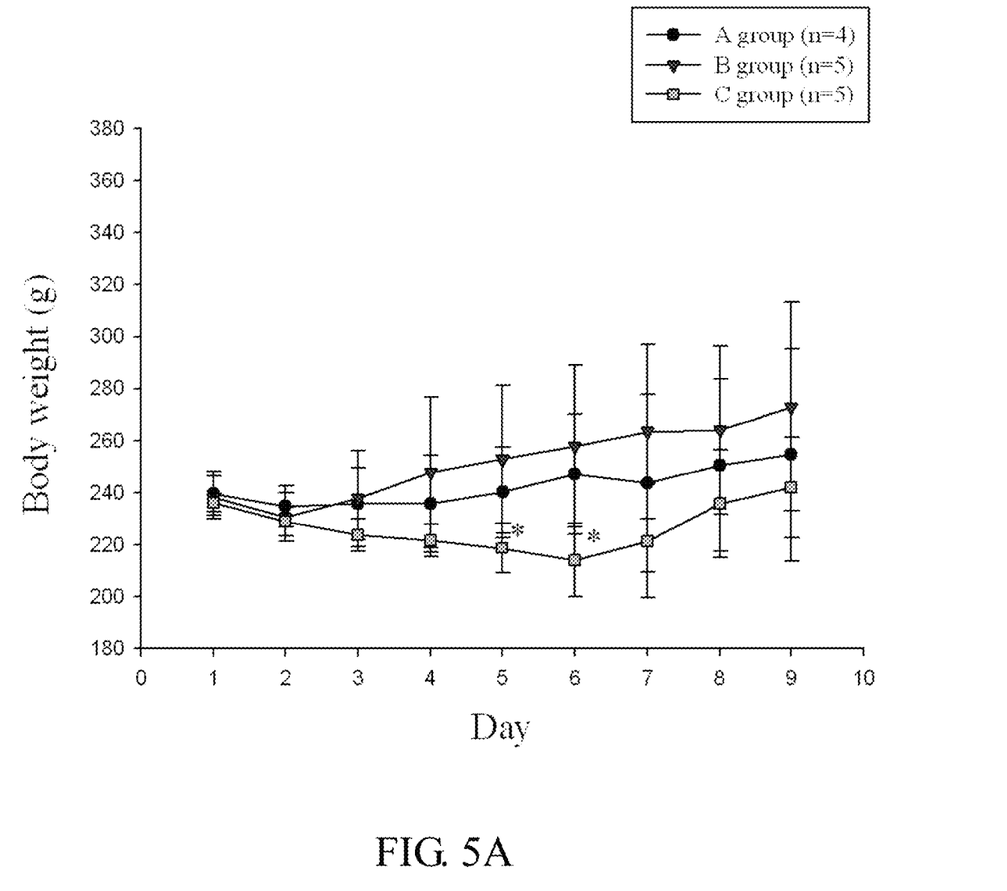
FIG. 5A shows effects of two categories of HAs on treating colitis indicated by average body weight of rats through test days 1 to 9.
Figure 5B:
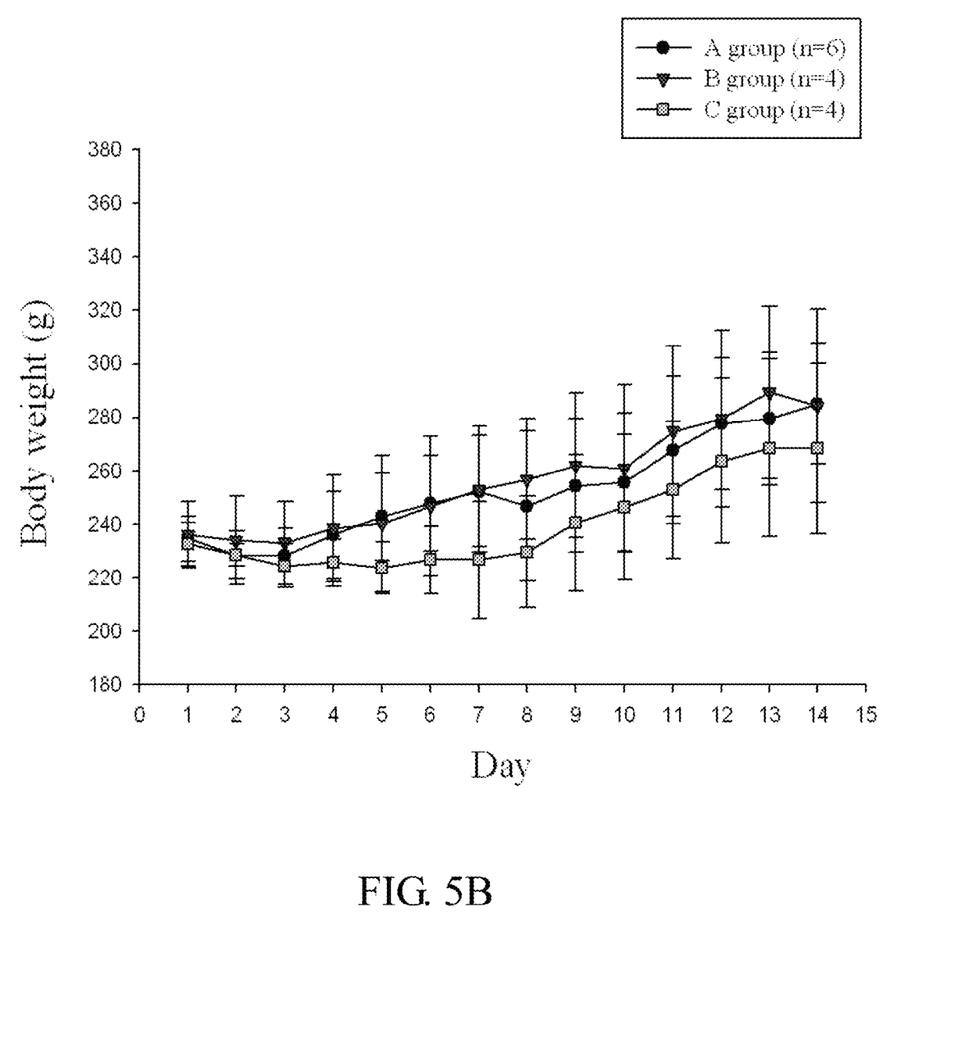
FIG. 5B shows effects of two categories of HAs on treating colitis indicated by average body weight of rats through test days 1 to 14.

The present invention presents IBD treated by HAs of different weight mixing ratios, which are indicated by average weight changes. In FIGS. 5A and 5B, group A represents a mixture of HMWHA and LMWHA in a mixing ratio of 8:2 by weight, whereas group B represents a mixture of HMWHA and LMWHA in a mixing ratio of 1:1 by weight. Group C represents a control group that HAs were replaced by PBS buffer. Although the statistic significance is only presented in days 5 and 6, the importance of the figure is in the trend of each group through day 1 to day 14. With days going, the trend shows that groups A and B both had relief effect on colitis, which also belongs to IBD. In average weight changes between control (group C) and HAs (groups A and B), treatment effect of colitis causes the average body weights of group by administered HAs were kept being higher than control group during the whole experimental period even till test day 14 (FIG. 5A). Interestingly, the trend also indicates that group B generally has a better treatment effect than that of group A, which means higher proportion of LMWHA has more efficient treating effect. This can support the technical feature of the present invention that uses HMWHA to compensate for LMWHA in order to prolong the effect.

Figure 6:
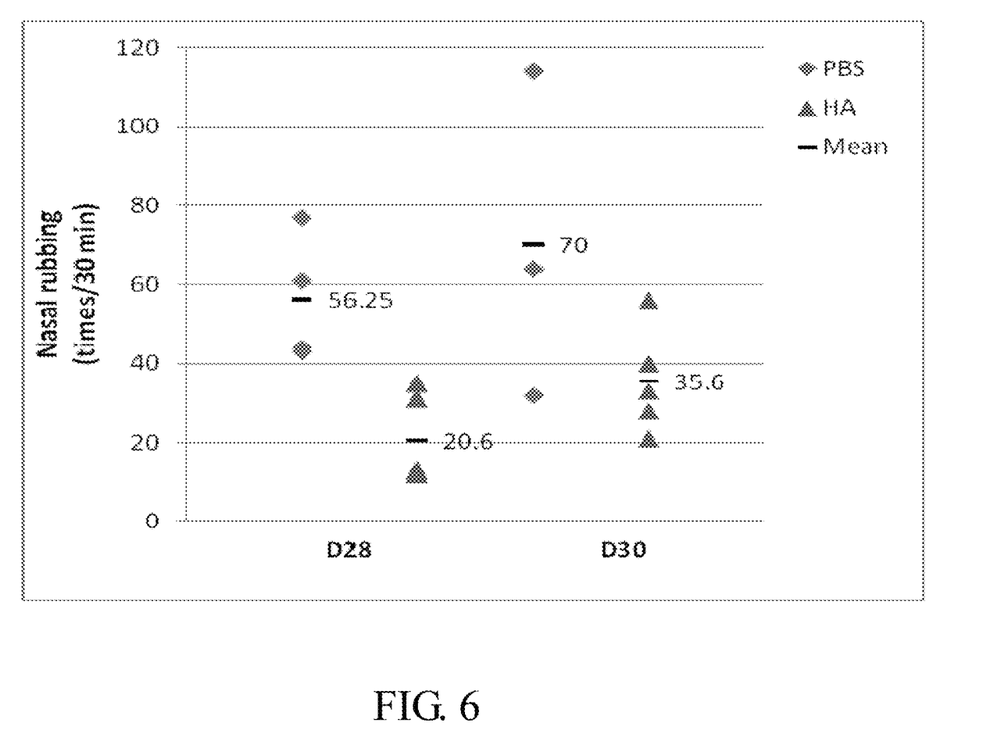
FIG. 6 shows the effect of HA sample on nasal rubbing induced by ovalbumin (10 µg/10 µl/nostril) in rats, demonstrating that significant difference between group HA and group control on day 28 (D28) was observed (*p<0.05).

The present invention takes advantage of nose rubbing as an easy index to indicate allergic symptom and the result of amelioration when the number of nose rubbing decreased. The result shows significant difference on day 28 (D28) between group control (only administered PBS) and group HA, which means allergic symptom has been successfully induced (FIG. 6). Though the result on day 30 (D30) does not have statistically significant difference, the allergic symptom still has obviously reduction between group control and group HA. Therefore, the trend of alleviating the allergic symptom has been highly proved by the result of administrating the HA mixture according to the present invention (FIG. 6).

The result may be slightly different in various experiments; however, the trend under overview of the present invention can be deduced to that the composition according to the present invention has ability to ameliorate mucosa related disease or disorder including allergic symptoms. In order to properly show the results, the present invention is proved by several related experiments with shorter test time; however, in actual application of the target of the present invention on mammals there would be a longer term than in the experiments. Therefore, based on theories and the results of the present invention, the HMWHA of the present invention shall be sufficient to support a long term assisting and/or compensating for the instant treatment effect of the LMWHA inside the body.

The preferred embodiment of treating IBS can be carried out by administering the mixture of the present invention as an adjuvant conjunctively used with a drug of antiallergic, antispasmodic, antidiarrheal, neurolytic, tranquilizer, narcotic analgesic, antidepressant or serotonin antagonist to a subject in need thereof.

In the preferred embodiment of oral formulation (for example enteric coated tablet), the enteric coating provides more resistance dissolution and digestion in the stomach, and after reaching the intestine and colon, the enteric coating will be dissolved and the HA mixture herein will be released to form a protection membrane at the inflammatory colon (the region uprising ascending or Transverse colon) in order to accelerate healing of the inflammatory region and also to prolong the treatment effect by long degradation rate.

In the preferred embodiment of suppository formulation, the suppository containing HA mixture herein may be inserted into the anus and the mixture will dissolve in the rectum and spread to other regions of the colon (for example the descending region) to form a protection membrane at the inflammatory colon in order to accelerate healing of the inflammatory region and also achieve sustained release effect.

In the preferred embodiment of perfusion formulation (for example enema), the HA mixture herein is the major active ingredient mixed with the excipient (for example phosphate buffered saline (PBS solution or suspension formulation)) directly used or in a soft tube to inject the above HA mixture into the colon. The HA mixture will be charged into the colon and spread to other regions of the colon (for example the descending region) to form a protection membrane at the inflammatory colon in order to accelerate the healing of the inflamed region and also achieve sustained release effect.

The more preferred embodiment of the subject being treated by the mixture used herein is mammal. The most preferred embodiment of the subject is human.

According to the above description, at least two species of pharmaceutically acceptable salt of the hyaluronic acids with different molecular weights are mixed to rapidly cover the wound or inflammatory surface and shorten the treatment period and prolong the degradation in order to prolong the coverage period. Thus, a faster treatment and a sustained release effect are achieved. The present invention provides an easier and safe way to treat aforementioned disorders or diseases and also a less costly way to assist related patients by supplying them with a better choice.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations which fall within the spirit and scope of the included claims. All matters set forth herein or shown in the accompanying drawings are to be interpreted in an illustrative and non-limiting sense.

DETAILED DESCRIPTION OF THE PREFERRED EMBODIMENTS

Example 1: The Degradation of HA in 1 U/Ml HAase

Procedure:

1. 0.25 g High molecule weight sodium hyaluronate powder (HHA; Mw: 2 MDa; Freda) and 0.25 g low molecule weight sodium hyaluronate powder (LHA; Mw: 0.35 MDa; Freda) were added into 50 ml PBS buffer (Phosphate buffered saline) respectively to form 0.5% solution, and then stirred for 6 hours until the powder was totally dissolved.

2. 0.05 g LHA powder and 0.2 g HHA powder (ratio 2:8; medium molecular weight sodium hyaluronate powder, MHA) were added into 50 ml PBS buffer, and then stirred for 6 hours until the powder was totally dissolved.

3. Mobile phase solution of GPC (Gel permeation chromatography) system was prepared by: (1) adding 35.49 g $Na_2HPO_4$ powder into 450 ml deionized distilled water (dd water) and stirred for 30 minutes in room temperature to form 0.5 M $Na_2HPO_4$ solution; and (2) adding 18 g $NaH_2PO_4$ powder into 250 ml dd water and stirred for 30 minutes in room temperature to form 0.5 M $NaH_2PO_4$ solution.

4. 1 U/ml HAase was prepared by dissolving HAase powder into PBS buffer in 4° C.

5. 2 ml HA sample, 1 ml 10 U/ml HAase and 7 ml PBS buffer were mixed for 3 minutes by vortex in 15 ml glass tube.

6. The tube was shaken by 50 rpm in water bath. 1 ml solution was taken after the 15, 30, 45, 60, 75, 90, 105, 120 minutes and then supplied with 1 ml HAase each time. Every 1 ml solution was filtered through 0.45 µm filter. 20 µl solution was injected into GPC system and then the diagram was recorded.

7. The situation of GPC system were (1) column: 2×GMPWx1 (TSK-gel); (2) mobile phase flow rate: 1 ml/min; (3) temperature: 30.

8. All values in the table were expressed as means of n observations. The histological index was analyzed by Student's t-test.

Result:

FIG. 2 shows the retention time of HAs by GPC diagram. The vertical axis represents the retention time in GPC, the horizontal axis represents the degradation time of HA in solution containing HAase. The horizontal dotted lines from up to down represent the retention time of 2 MDa, 1 MDa, 350 KDa and 17 KDa HAs, respectively. The retention time was obviously increased followed with the increased degradation of all three HAs. After 15 minutes of degradation, the average Mw of HHA and MHA were degraded to about 1 MDa. After 37 minutes of degradation, the average Mw of HHA and MHA were degraded to about 350 KDa. After 90 minutes of degradation, the average molecular weights of HHA, MHA and LHA were degraded such that no obvious difference exists among the average molecular weights, which were all larger than 17 KDa.

Example 2: The Degradation of HA in 0.1 N HCl

Procedure:
1. LHA, MHA and HHA were prepared as the same as Example 1.
2. Mobile phase solution of GPC system was prepared as the same as Example 1.
3. Artificial gastric juice (0.1 N HCl) was prepared by mixing 5.72 ml 17.5 N HCl and 90 ml dd water and stirred for 10 minutes as a stocking solution.
4. 2 ml of HHA, MHA and LHA were mixed with 8 ml artificial gastric juice, respectively in a 15 ml glass tube and by vortex for 3 minutes.
5. The tube was shaken by 50 rpm in 37° C. water bath. 1 ml solution was taken after the 6, 12, 24, 48 hours and then supplied with 1 ml artificial gastric juice each time. Every 1 ml solution was filtered through 0.45 μm filter. 20 μl solution was injected into GPC system and then the diagram was recorded.
6. All values in the table were expressed as means of n observations. The histological index was analyzed by Student's t-test.

Result:
FIG. 3 shows the retention time of HAs in GPC diagram. The vertical axis represents the retention time in GPC, the horizontal axis represents the degradation time of HA in artificial gastric juice. The horizontal dotted lines from up to down represent the retention time of 2 MDa, 1 MDa, 350 KDa and 17 KDa HAs, respectively. The retention time was slowly increased followed by the increased degradation of all three HAs. After 7 hours of degradation, the average molecular weights of HHA and MHA were degraded to about 1 MDa. After 31 hours of degradation, the average Mw of MHA was degraded to about 350 KDa. After 35 hours of degradation, the average Mw of HHA was degraded to about 350 KDa. The aforementioned data all indicate that HA was slowly degraded in the artificial gastric juice whereas the average molecular weights of HHA and MHA were larger than 1 MDa after 6 hours of degradation, and the average molecular weights of HHA and MHA were larger than 350 KDa after 24 hours of degradation.

Example 3: The Adhesion of HA in Colon Tissue (IVIS Image System-Vision 3)

Procedure:
1. LHA and HHA were prepared as the same as Example 1. MHA (MHA; Mw: 1 MDa; Freda) were added into 50 ml PBS buffer, and then stirred for 6 hours until the powder was totally dissolved and ready for use in the following steps.
2. Fluorescent HA (HA-f) was prepared by (1) 0.39 g MES free acid (2-(N-morpholino) ethanesulfonic acid, Calbiochem) and was dissolved in 100 ml dd water. (2) Solution A: 65 mg fluroresceinamine powder, (isomer I, Fluka) was dissolved in 9 ml 95% EtOH solution and then stirred for 10 minutes under a condition that light was prohibited. (3) Solution B: 359 mg EDC powder (N-(3-Dimethylamino propyl)-N-ethyl carbodiimide hydrochloride, Sigma) was dissolved in 9 ml MES buffer and then stirred for 10 minutes. (4) Solution C: 216 mg NHS powder (N-Hydroxysuccinimde, Sigma) was dissolved in 9 ml MES buffer and then stirred for 10 minutes. (5) 3 ml Solution A was slowly dropped into 50 ml 0.5% HA solution and then stirred for 10 minutes under a condition that light was prohibited. (6) 3 ml Solution B and 5 ml Solution C were separately dropped into the solution of step (5) and then stirred for 10 minutes under a condition that light was prohibited. (7) 0.02 M MES buffer was slowly added into the solution of step (6) until the volume reached 100 ml and then stirred for 24 hours at room temperature under a condition that light was prohibited. (8) The product after reaction was poured into a dialysis tubing (MW: 12000~14000) in 5 L dd water as a dialysis solution and then stirred for 5 days at 4 under a condition that light was prohibited with dialysis solution being changed every 12 hours until the dialysis solution had no fluorescence. (9) The liquid after dialysis was allocated into 50 c.c. plastic centrifuge tubes and then reserved at −20° C. refrigerator overnight followed by drying in a freeze-drying machine under a condition that light was prohibited. (10) The dried HA-f powder was reserved at −20° C. refrigerator. (11) 50 mg HA-f powder was slowly added into 10 ml PBS buffer and then stirred for 6 hours until the powder was totally dissolved.
3. Colon tissue of SD-rat (Sprague-Dawley Rat) aged 7-8 weeks was cut by scalpel and then washed by PBS buffer followed by being cut to 3-4 cm long with soaking in PBS buffer finally.
4. Injured colon tissue was prepared by brushing by toothbrush for 20 times longitudinally and then soaking in PBS buffer.
5. Normal and injured colon tissues were put into a 12-well plate and then 1 ml 0.5% HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times.
6. Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.
7. All values in the table are expressed as means of n observations. The histological index was analyzed by Student's t-test.

Result: The fluorescent index was quantified and arranged as in FIG. 4. The fluorescent index of normal colon tissue was defined as 1. The other colon tissues tests were calibrated by the defined value. The result showed that the HAs with the same average Mw were absorbed in the injured colon tissues obviously higher than in the normal colon tissues ($P<0.01$). In comparing the difference between HAs of three different average molecular weights absorbed in the injured colon tissues, the fluorescent index of absorption of 350 KDa HA by the injured colon tissues was obviously higher than HAs of the other two average molecular weights (2 MDa and 1 MDa). Further, the fluorescent index of absorption of 1 MDa HA by even normal or injured colon tissues was higher than 2 MDa HA.

Example 4: The Body Weight Change of Rat with or without Administration of HA Aimed at Colitis Procedure:

1. Test purpose: to induce the colitis in the SPF grade SD (Sprague-Dawley) rats with the TNBS in order to evaluate the effect for treating or preventing colitis by two kinds of mixing HAs differing in weight proportion.

2. Test objective: IBD98, comprising LMWHA and HMWHA, whereas the HMWHA was 2 million Da and the LMWHA was 350 kilo Da, mixed in the ratio of 8:2 and 1:1 by weight which were categorized into group A and group B, respectively, and dissolved in PBS solution to produce a concentration of 0.125% (w/v).

3. Method: (1) Test target: Rats aged 8 weeks were selected, and classified into three groups: group A represented mixing ratio of 8:2; group B represented mixing ratio of 1:1; group C was treated by PBS instead of HA. (2) Animal test: all rats of the treating group were fasted for 2 days; in test day 1, the rats were anesthetized for administrating 1 ml of TNBS (50 mg/mL) via the rectum; through test days 4 to 14, administering 1 ml of two categories of IBD98 via the rectum in groups A and B; in test day 9, the body weight changes of half rats in groups A and B were observed. And the body weight changes of the other half rats were observed in day 14. All rats of the control group were fasted for 2 days; in test day 1, the rats were anesthetized for administrating 1 ml of TNBS (50 mg/mL) via the rectum; in test days 4 to 14, administering 1 ml of PBS via the rectum; in test day 9, the body weight changes of half rats in group C were observed. And the body weight changes of the other half rats were observed in day 14.

Result:

1. Inflammatory index: the present invention used changes of average body weight as an index to view the amelioration of colitis (IBD). The change of the body weight is a convenient and direct index to check the treatment result.

2. The trend showed groups A and B both had relief effects on colitis which also represented IBD through day 1 to day 14 (FIGS. 5A and 5B). In average weight changes between control and HAs, treatment effect of colitis caused the average body weights of group by administered HAs to be kept higher than those of control group during the whole experimental period even till test day 14 (FIG. 5B).

Example 5: HA Effect on Allergic Disease

Procedure:

1. Test purpose: to induce the allergic disease, herein rhinitis, in the SPF grade SD (Sprague-Dawley) rats.

2. Test objective: IBD98, comprising LMWHA and HMWHA, whereas the average molecular weight of HMWHA is 2 million Da and the average molecular weight of LMWHA is 350 kilo Da, mixed in the ratio of 1:1 by weight dissolved in PBS solution to produce a HA solution at a concentration of 0.125% (w/v).

3. Method: (1) Test target: Nine rats aged 8 weeks were selected, and classified into two groups randomly: Control group (PBS) consisted of 4 rats and the test group (HA) consisted of 5 rats. (2) Animal test: during test day 1 to day 7, the rats were intra-peritoneally (IP) injected with physiological saline containing ovalbumin (1 mg) and alum (10 mg) in each day; just observing through test day 8 to day 13; during test day 14 to day 27, dripping ovalbumin in saline solution (10 μg/10 μl/nostril) into bilateral nasal cavities by micropipette. The effect of HA on the nasal symptoms after antigen challenge were evaluated with rats on day 28 (D28) and day 30 (D30) after general sensitization. Before 1 hour of the instillation of ovalbumin, the animals were dripped with the HA solution or PBS (25 μL/nostril). After nasal instillation of ovalbumin in saline (10 μg/10 μL/nostril) into the bilateral nasal cavities, the animals were placed in the observation cage (1 animal/cage), and nasal rubbing were counted for 30 minutes. The nasal rubbing frequency was calculated as the times of nasal rubbing per 30 minutes.

Result:

1. Allergic amelioration index: the present invention used the nose rubbing frequency as an index of allergic amelioration.

2. The effect of the HA sample on the antigen-induced nasal symptoms were shown in FIG. 6. The average nasal rubbing frequency induced by ovalbumin was 56.25±16.1 times/30 minutes on day 28 (D28) and 70.0±41.3 times/30 minutes on day 30 (D30). Compared with the control group, nasal rubbing was reduced significantly by the HA solution on day 28 and obviously reduced on day 30.

What is claimed is:

1. A method for treating a respiratory mucosa related disorder or disease comprising:
    administering to a subject in need thereof a therapeutically effective amount of a hyaluronic acid mixture, consisting of
    a low average molecular weight hyaluronic acid (LMWHA) having an average molecular weight (Mw) in a range from 0.1 million Da to 0.5 million Da,
    a high average molecular weight hyaluronic acid (HMWHA) having an average molecular weight (Mw) in a range from 1.5 million Da to 5 million Da, excluding 1.5 million Da; and
    an excipient, wherein the excipient, the LMWHA and the HMWHA are admixed to formulate an administrating dosage form for nose, respiratory tract, or topical use, wherein the administrating dosage form for topical use is selected from the group consisting of inhalation and drop;
    wherein a difference between the average Mw of LMWHA and the average Mw of HMWHA is at least 1.5 million Da, and a mixing ratio of the LMWHA to the HMWHA is in a range from 20:80 to 80:20 by weight, such that the degradation of HMWHA effectively compensates for the degradation of LMWHA;
    wherein the respiratory mucosa related disorder or disease is allergic rhinitis.

2. The method of claim 1, wherein the average Mw of HMWHA is between 1.5 million Da and 3.5 million Da.

3. The method of claim 2, wherein the average Mw of HMWHA is between 1.5 million Da and 2.5 million Da.

4. The method of claim 1, wherein the mixing ratio of the LMWHA to HMWHA is 1:1 by weight.

5. The method of claim 1, wherein the therapeutically effective amount is at a range from 0.05 mg/ml to 50 mg/ml.

6. The method of claim 5, wherein the therapeutically effective amount is at a range from 0.05 mg/ml to 5 mg/ml.

* * * * *